US012763221B2

(12) United States Patent
Shapira et al.

(10) Patent No.: US 12,763,221 B2
(45) Date of Patent: Oct. 13, 2026

(54) ADAPTING ARRAY LAYOUTS TO ACCOUNT FOR TUMOR PROGRESSION

(71) Applicant: Novocure GmbH, Root (CH)

(72) Inventors: Nadav Shapira, Haifa (IL); Brian Berger, New York, NY (US)

(73) Assignee: Novocure GmbH, Baar (CH)

( * ) Notice: Subject to any disclaimer, the term of this patent is extended or adjusted under 35 U.S.C. 154(b) by 0 days.

(21) Appl. No.: 18/675,714

(22) Filed: May 28, 2024

(65) Prior Publication Data

US 2025/0006382 A1 Jan. 2, 2025

Related U.S. Application Data

(60) Provisional application No. 63/523,853, filed on Jun. 28, 2023.

(51) Int. Cl.
*G16H 50/50* (2018.01)
*A61N 1/36* (2006.01)
*G16H 50/20* (2018.01)

(52) U.S. Cl.
CPC ............. *G16H 50/50* (2018.01); *G16H 50/20* (2018.01); *A61N 1/36002* (2017.08)

(58) Field of Classification Search
None
See application file for complete search history.

(56) References Cited

U.S. PATENT DOCUMENTS 7,565,205 B2 7/2009 Palti
7,599,746 B2 10/2009 Palti
9,370,304 B2 * 6/2016 Cao ........................ G06T 7/0016
2018/0160933 A1 6/2018 Urman et al.
2020/0023179 A1 1/2020 Bomzon et al.
2021/0187277 A1 6/2021 Wasserman et al.
2021/0196943 A1 7/2021 Shamir et al.
2022/0305285 A1 9/2022 Czeizler et al.
2022/0313992 A1 * 10/2022 Wasserman ........ A61N 1/36002
2022/0400251 A1 * 12/2022 Fisher .................... G16H 50/20
2023/0005140 A1 * 1/2023 Ferl ........................... G06T 7/11

OTHER PUBLICATIONS

Guo et al. Cancer (2022) vol. 14: 23 pages.*
Trusheim et al. CNS Oncol. (2017) vol. 6: pp. 29-43.*
Jin et al. in Medical Image Analysis (2021) vol. 68:13 pages.*
Korshoej et al. in PLoS One (2018) vol. 13(8):16 pages.*
V. Contie, "Machine learning approach detects brain tumor boundaries," NIH Research Matters, Dec. 13, 2022, www.nih.gov/news-events/nih-research-matters/machine-learning-approach-detects-brain-tumor-boundaries. 4 pages.

* cited by examiner

*Primary Examiner* — Lori A. Clow
(74) *Attorney, Agent, or Firm* — McCarter & English, LLP; Michael A. Sartori

(57) ABSTRACT

A computer-implemented method comprising: obtaining a three-dimensional model of a subject, the model comprising voxels; identifying a gross tumor volume for the three-dimensional model, the gross tumor volume representing a current location of a tumor in the subject; identifying a primary clinical target volume for the three-dimensional model, the primary clinical target volume having a larger volume than the gross tumor volume, the primary clinical target volume representing an approximation of the current location of the tumor in the subject; identifying a predictive clinical target volume for the three-dimensional model, the predictive clinical target volume having a larger volume than the primary clinical target volume, the predictive clinical target volume representing a predicted future location of the tumor in the subject; and selecting at least one transducer layout for delivering tumor treating fields to the subject based on the primary clinical target volume and the predictive clinical target volume.

22 Claims, 4 Drawing Sheets

ADAPTING ARRAY LAYOUTS TO ACCOUNT FOR TUMOR PROGRESSION

CROSS-REFERENCE TO RELATED APPLICATIONS

This application claims priority to U.S. Provisional Application No. 63/523,853 filed Jun. 28, 2023, the contents of which is incorporated by reference herein in its entirety.

BACKGROUND

Tumor treating fields (TTFields) are low intensity alternating electric fields within the intermediate frequency range (for example, 50 kHz to 1 MHz), which may be used to treat tumors as described in U.S. Pat. No. 7,565,205. TTFields are induced non-invasively into the region of interest by transducers placed on the patient's body and applying AC voltages between the transducers. Conventionally, transducers used to generate TTFields include a plurality of electrode elements comprising ceramic disks. One side of each ceramic disk is positioned against the patient's skin, and the other side of each disc has a conductive backing. Electrical signals are applied to this conductive backing, and these signals are capacitively coupled into the patient's body through the ceramic discs. Conventional transducer designs include arrays of ceramic disks attached to a subject's body via a conductive skin-contact layer such as a hydrogel. AC voltage is applied between a pair of transducers for an interval of time to generate an electric field with field lines generally running in the front-back direction. Then, AC voltage is applied at the same frequency between at least another pair of transducers for another interval of time to generate an electric field with field lines generally running in the right-left direction. The system then repeats this two-step sequence throughout the treatment.

DESCRIPTION OF EMBODIMENTS

This application describes exemplary techniques to computationally select and determine at least one transducer array layout for delivering TTFields on the subject.

Traditionally in tumor treatment, radiation is applied to treat where a tumor is identified and located. Severe side effects may occur when applying the radiation to larger areas based on predictive spread. For example, the inherent toxicity of radiation treatment may cause side effects that may outweigh the benefits from treating a tumor. Further, the human body may also have a lifetime maximum limit to the effectiveness of radiation treatment. Moreover, applying radiation to a predictive area where the tumor may spread may reduce the effectiveness of subsequent treatment with radiation.

As an alternative or supplemental treatment, TTFields may be introduced and delivered to the subject's body, which may have less side effects and more flexibility in term of tailoring a tumor treatment plan. In general, in order to apply TTFields to the subject's body, one or more pairs of transducers are positioned on the subject's body. Generally, it is preferred that there are at least two pairs of transducers. Transducers used to apply TTFields to the subject's body often include multiple electrode elements coupled together on a substrate. Determining the predictive spread of the tumor and a corresponding location where to place the transducers on the subject involves using very large data sets and computationally solving complex algorithms that can take a significant amount of time.

The inventors discovered computational techniques to determine one or more predictive clinical target volumes for a tumor, wherein the predictive clinical target volume represents a predicted future location of the tumor in the subject. The treatment of the predicted future location of the tumor in the subject may reduce the likelihood of the tumor expanding and/or another tumor forming in the subject. The inventive techniques are particularly integrated into a practical application. With the inventive techniques, more locations on the subject can be involved in tumor treatment with less side effects compared to when using radiation alone. With the inventive techniques, more transducer locations may be determined much quicker than with conventional techniques. In addition, the inventive techniques allow flexible deployment and combination of tumor treatment methods and dosage use.

Figure 1:
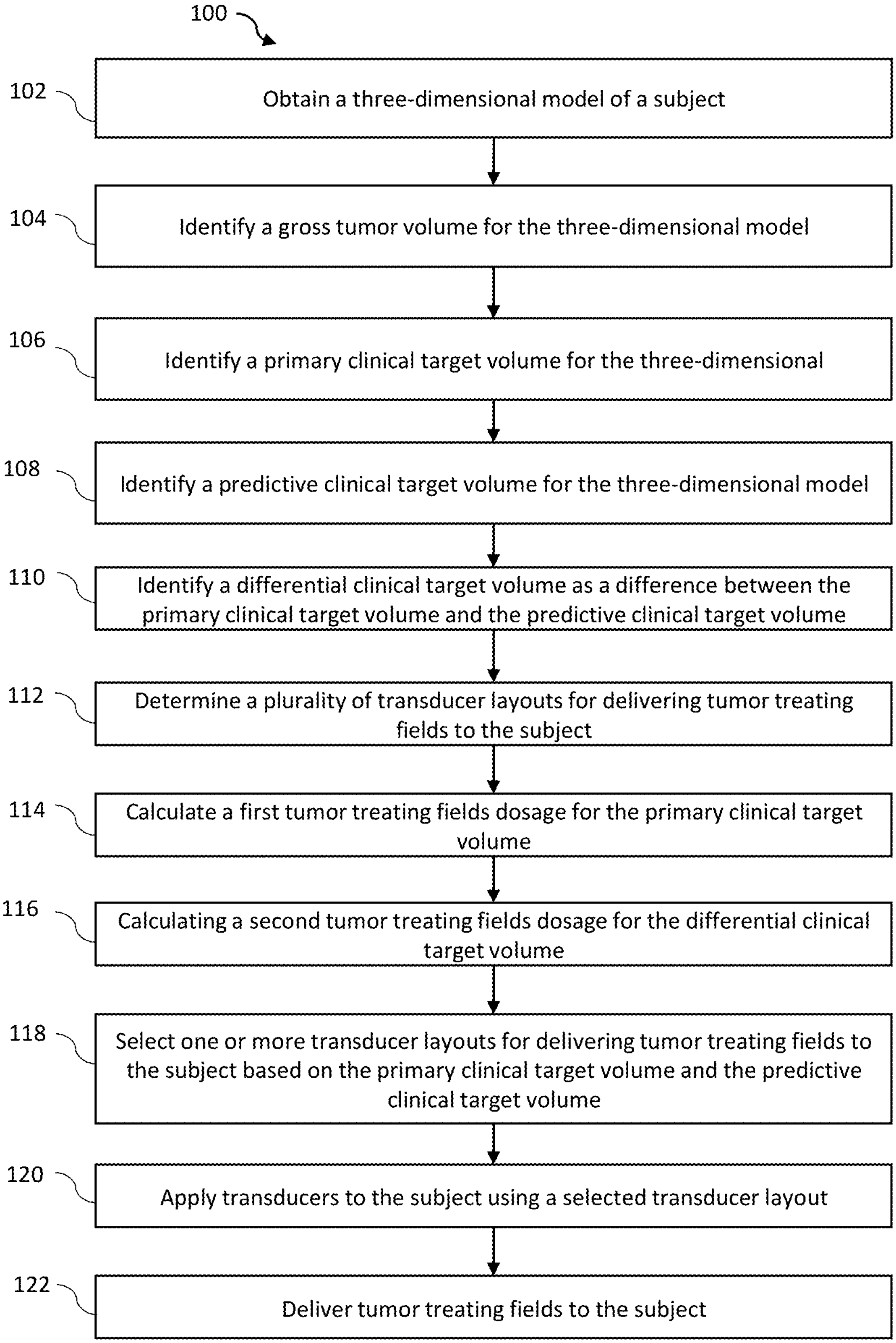
FIG. 1 depicts an example method for determining transducer locations for delivering TTFields to the subject.

FIG. 1 depicts an example computer-implemented method 100 for selecting at least one transducer array layout for delivering TTFields to the subject. The method 100 may be implemented by a computer, the computer including one or more processors and memory accessible by the one or more processors, the memory storing instructions that when executed by the one or more processors cause the computer to perform the steps of the method 100. Modifications, additions, or omissions may be made to method 100.

The method 100 includes, at step 102, obtaining a three-dimensional (3D) model of the subject. The model includes voxels. Each voxel of the model may be assigned a type of tissue (e.g., bone, organs, fluid, skin, or tumor) and/or an electrical conductivity associated with the type of tissue. In one example, the model of the subject may represent a head of the subject. In another example, the model of the subject may represent a torso of the subject. Other body parts of the subject may be represented in the model of the subject in other embodiments.

The model may be obtained using image data, for example, via a computer identifying the different types of tissue from the image data. The image data may include one or more medical images of a portion of the subject's body (e.g., X-ray images, magnetic resonance imaging (MRI), computerized tomography (CT) images, ultrasound images, or any image providing an internal view of the subject's body). Each medical image may include an outer shape of a portion of the subject and a region corresponding to the region of interest (e.g., tumor) within the subject. The three-dimensional model may be obtained, for example, from computer memory locally or over a network.

At step 104, the method 100 may include identifying a gross tumor volume (GTV) for the three-dimensional model. The gross tumor volume may be the gross palpable or visible/demonstrable extent and location of malignant growth. The gross tumor volume may include all disease on physical examination with endoscopy and imaging. The gross tumor volume may represent one or more current locations of at least one tumor in the subject. In an example, the gross tumor volume may be based on user input To assist in describing the method 100, FIGS. 2A-2E are also discussed. FIGS. 2A-2E depict an example of various target volumes in a two-dimensional view, such as target volumes in a slice through a medical image. For convenience, the entirety of the slice is not shown and, instead, just the target volumes are shown. For example, in FIG. 2A, a gross tumor volume (GTV) 202 may represent a current location of the tumor in the subject.

At step 106, the method 100 may include identifying a primary clinical target volume (CTV) for the three-dimensional model. The primary clinical target volume may include the gross tumor volume and a proximal margin beyond the identified gross tumor volume. The primary clinical target volume may represent an approximation of the current location of the at least one tumor in the subject. In one example, the primary clinical target volume may represent a location in the subject to be treated, for example, with radiation and/or TTFields. In an example, the approximation of the current location of the at least one tumor in the subject represented by the primary clinical target volume accounts for at least one of an error in identifying the gross tumor volume or a portion of the tumor undetected in the gross tumor volume. In an example, the primary clinical target volume may be larger than the gross tumor volume. In an example, the primary clinical target volume may be based on user input.

Figure 2A:
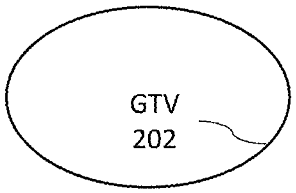
FIGS. 2A-2E depict examples of various target volumes.
Figure 2B:
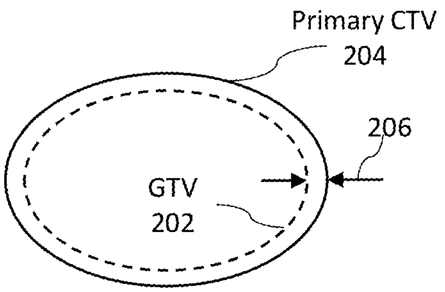

In FIG. 2B, a primary clinical target volume (CTV) 204 may represent an approximation of the current location of the tumor in the subject. In an example, the primary clinical target volume 204 may have approximately a same shape as the gross tumor volume 202 (shown in dashed line in FIG. 2B), but have a larger volume than the gross tumor volume 202. In an example, a distance 206 between a surface of the primary clinical target volume 204 and a surface of the gross tumor volume 202 may be between approximately 1 mm to approximately 5 mm, or between approximately 1 mm to approximately 10 mm. In an example, the primary clinical target volume 204 may be larger than the gross tumor volume 202 by between approximately 1% to approximately 5%, or by between approximately 2% to approximately 3%. In one example, a volume between the primary clinical target volume 204 and the gross tumor volume 202 may be a para-tumor boundary zone.

At step 108, the method 100 may include identifying at least one predictive clinical target volume for the three-dimensional model. In one example, step 108 may include identifying one predictive clinical target volume, and/or a plurality of predictive clinical target volumes including the one predictive clinical target volume. In an example, the at least one predictive clinical target volume may include a plurality of non-contiguous volumes. The at least one predictive clinical target volume may represent at least one predicted future location and potential spread of the at least one tumor in the subject. In an example, the predictive clinical target volume may be based on a progression of the tumor in the subject over a period of time, where the period of time may be, for example, 1 month to 6 months.

In an example, the predictive clinical target volume may be determined using a predictive model for predicting the occurrence and location of a tumor similar to the tumor in the subject. For example, the predictive model may determine a future location of the tumor in the subject based on the current location of the tumor and at least one of tumor type/indication, initial growth rate of the tumor, initial location of the tumor, and subject's biographic data. For example, the predictive model may determine a future location of the tumor in the subject based on the current location of the tumor and at least one of the subject's medical background, an indication or type of the tumor, a subtype or classification of the tumor, and past progression of the tumor. In one example, the predictive model may be a trained machine learning model that is trained by a plurality of tumors similar to the tumor in the subject. In an example, the predictive model may be trained to predict a future location of the tumor in the subject and/or may also be trained to predict a future location of a tumor similar to the tumor in the subject.

Figure 2C:
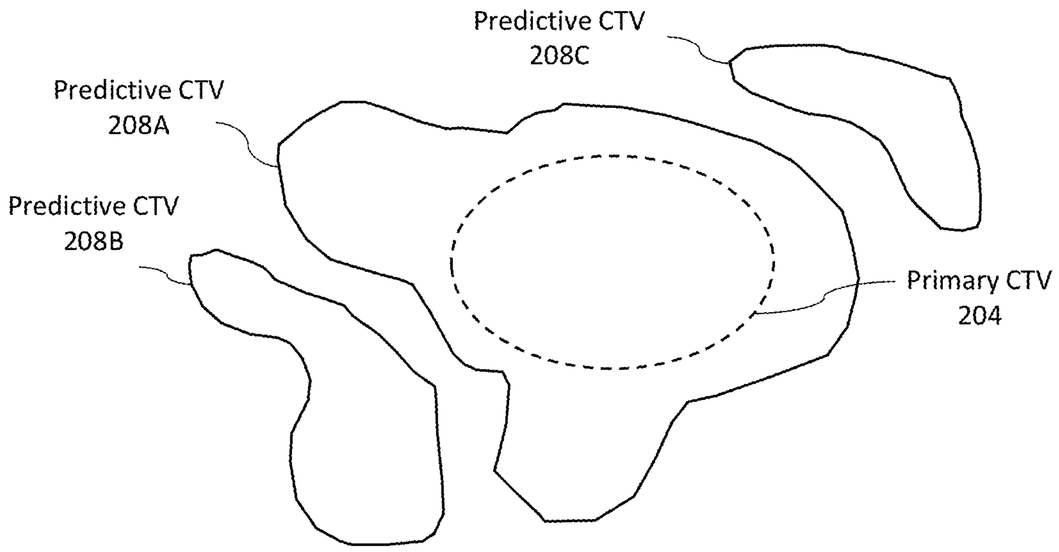

In FIG. 2C, a predictive clinical target volume 208A, 208B, and 208C (collectively 208) may represent a predicted future location of the tumor in the subject. In an example, the predictive clinical target volume 208 has a larger volume and/or a different shape than the primary clinical target volume 204 (shown in dashed line in FIG. 2C). The predictive clinical target volume may include a plurality of non-contiguous volumes. In particular, the predictive clinical target volume may include a plurality of non-contiguous volumes, for example, 208A, 208B, and 208C.

At step 110, the method 100 may include identifying a differential clinical target volume as a difference between the primary clinical target volume and the predictive clinical target volume. In an example, the differential clinical target volume may include a plurality of non-contiguous volumes.

Figure 2D:
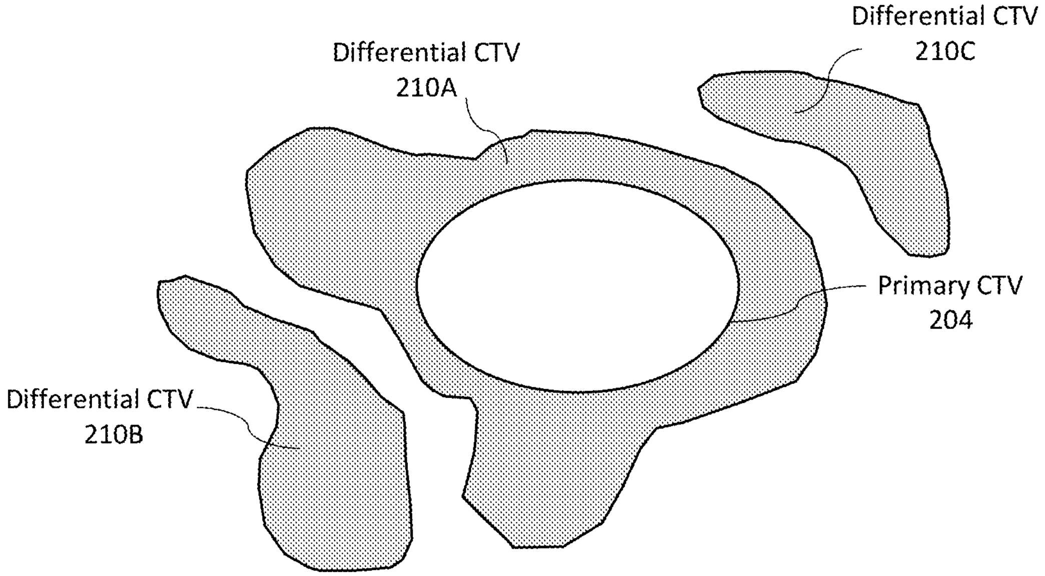

In FIG. 2D, a differential clinical target volume 210A, 210B, and 210C (collectively 210) may represent a difference between the primary clinical target volume 204 and the predictive clinical target volume 208. In FIG. 2D, the differential clinical target volume 210 is depicted as the shaded region. The differential clinical target volume may include a plurality of non-contiguous volumes, for example, 210A, 210B, and 210C.

Figure 2E:
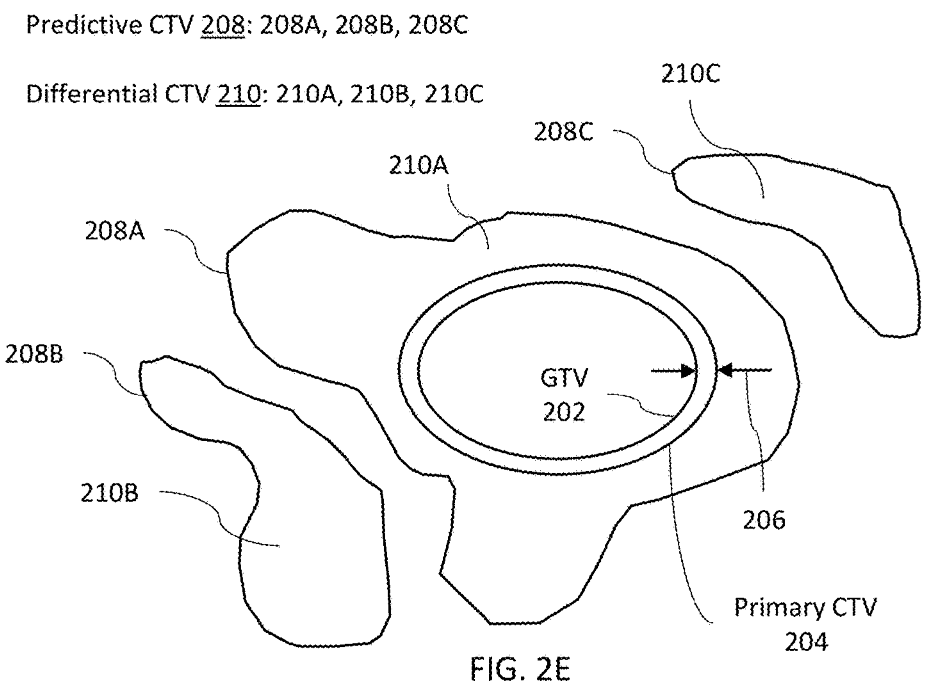

In FIG. 2E, the various target volumes in FIGS. 2A, 2B, 2C, and 2D are depicted together.

At step 112, the method 100 may include determining a plurality of transducer array layouts for delivering TTFields to the subject. In an example, the transducer array layouts in the plurality of transducer array layouts differ by at least one of location on the subject, size of the transducer, shape of the transducer, number of electrodes of the transducer, size of electrodes of the transducer, or shape of electrodes of the transducer. In an example, step 112 includes determining four transducer array layouts.

At step 114, the method 100 may include calculating a first TTFields dosage for the primary clinical target volume. Step 114 may include calculating a first TTFields dosage for each determined transducer array layout. In an example, the first TTFields dosage for the primary clinical target volume may be a pre-determined minimum dosage for tumors similar to the tumor of the subject. In an example, the first TTFIelds dosage for the primary clinical target volume may be based on a local average field intensity and/or a local power density within a target range. In an example, the first TTFIelds dosage for the primary clinical target volume may be based on a local field intensity and/or a local power density within the primary clinical target volume.

At step 116, the method 100 may include calculating a second TTFields dosage for the differential clinical target volume. In an example, the second TTFields dosage for the differential clinical target volume may be less than the pre-determined minimum dosage. In an example, the second TTFields dosage for the differential clinical target volume may be calculated as a percentage of the first TTFields dosage for the primary clinical target volume. In an example, the second TTFields dosage for the differential clinical target volume and the first TTFields dosage for the primary clinical target volume are not identical. For example, the second TTFields dosage for the differential clinical target volume may be less than or larger than the first TTFields dosage for the primary clinical target volume. In an example, the second TTFields dosage for the differential clinical target volume may be a pre-determined minimum dosage for tumors similar to the tumor of the subject. In an example, the second TTFIelds dosage for the differential clinical target volume may be based on a local average field intensity and/or a local power density within a target range. In an example, the second TTFIelds dosage for the differential clinical target volume may be based on a local field intensity and/or a local power density within the predictive clinical target volume.

As an example, calculating the dosage of TTFields treatment is further described in more detail in U.S. Patent Application Publication No. 2020/0023179, entitled "USING POWER LOSS DENSITY AND RELATED MEASURES TO QUANTIFY THE DOSE OF TUMOR TREATING FIELDS (TTFIELDS)" and U.S. Patent Publication No. 2021/0196943, entitled "METHODS, SYSTEMS, AND APPARATUSES FOR FAST APPROXIMATION OF ELECTRIC FIELD DISTRIBUTION," the entire contents of both of which are incorporated by reference herein. It should be appreciated that these calculations in steps 114 and 116 involve solving complex algorithms using large data sets associated with the subject and, as such, require the use of a computer apparatus, as the human mind is not capable of performing the required calculations.

Additionally, the first and second TTFields dosage may be calculated individually. For example, the first TTFields dosage may be calculated assuming the second TTFields dosage is not applied simultaneously with the first TTFields dosage. In another example, the second TTFields dosage may be calculated assuming the first TTFields dosage is not applied simultaneously with the second TTFields dosage.

In an example, the differential clinical target volume may include a plurality of non-contiguous volumes. As such, a TTFields dosage may be determined for each of the non-contiguous volumes of the differential clinical target volume. In an example, at least two of the non-contiguous volumes of the differential clinical target volume have different TTFields dosages. In another example, a non-zero TTFields dosage may be determined for each of the non-contiguous volumes of the differential clinical target volume.

In an example, two or more predictive clinical target volumes may be determined. A weight may be assigned to each of the predictive clinical target volumes, where each weight represents a likelihood of the predicted future location of the tumor in the subject for the respective the predictive clinical target volume. For example, as shown in FIG. 2C, a first weight of a first predictive clinical target volume 208A may be larger than a second weight of a second predictive clinical target volume 208B, and in this situation, the first predictive clinical target volume 208A may be assigned a larger TTFields dosage than the second predictive clinical target volume 208B. A second weight of a second predictive clinical target volume 208B may be the same as a third weight of a third predictive clinical target volume 208C, and in this situation, the second predictive clinical target volume 208B may be assigned a same TTFields dosage as the third predictive clinical target volume 208C.

At step 118, the method 100 may include selecting at least one transducer array layout for delivering TTFields to the subject, wherein the at least one transducer array layout may be selected from the plurality of transducer array layouts determined at step 112. In one example, the selection may be based on the primary clinical target volume and the predictive clinical target volume. In one example, the selection may be based on the primary clinical target volume, the plurality of predictive clinical target volumes, and the weights for the plurality of predictive clinical target volumes. In one example, the selection may be based on a calculated first and/or second TTFields dosage. In one example, the selection may be based on a desired intensity for one or more of a primary CTV or a differential CTV. Using the selected at least one transducer array layouts, a physician may select a transducer array layout that achieves a minimum dosage for treating the tumor of the subject.

At step 120, the method 100 may include applying transducers to the subject using a selected transducer array layout. More details of step 120 are described in accordance with FIGS. 4A, 4B, and 5.

At step 122, the method 100 may include delivering the TTFields to the subject based on the selected transducer array layout. In particular, when delivering the TTFields, the subject may take one or more breaks from one treating area, for example, the primary clinical target volume, and the selected array layout may be moved to focus on another treating area, for example, a predicted clinical target volume while skin of the previous treating area recovers.

Exemplary Apparatuses

Figure 3:
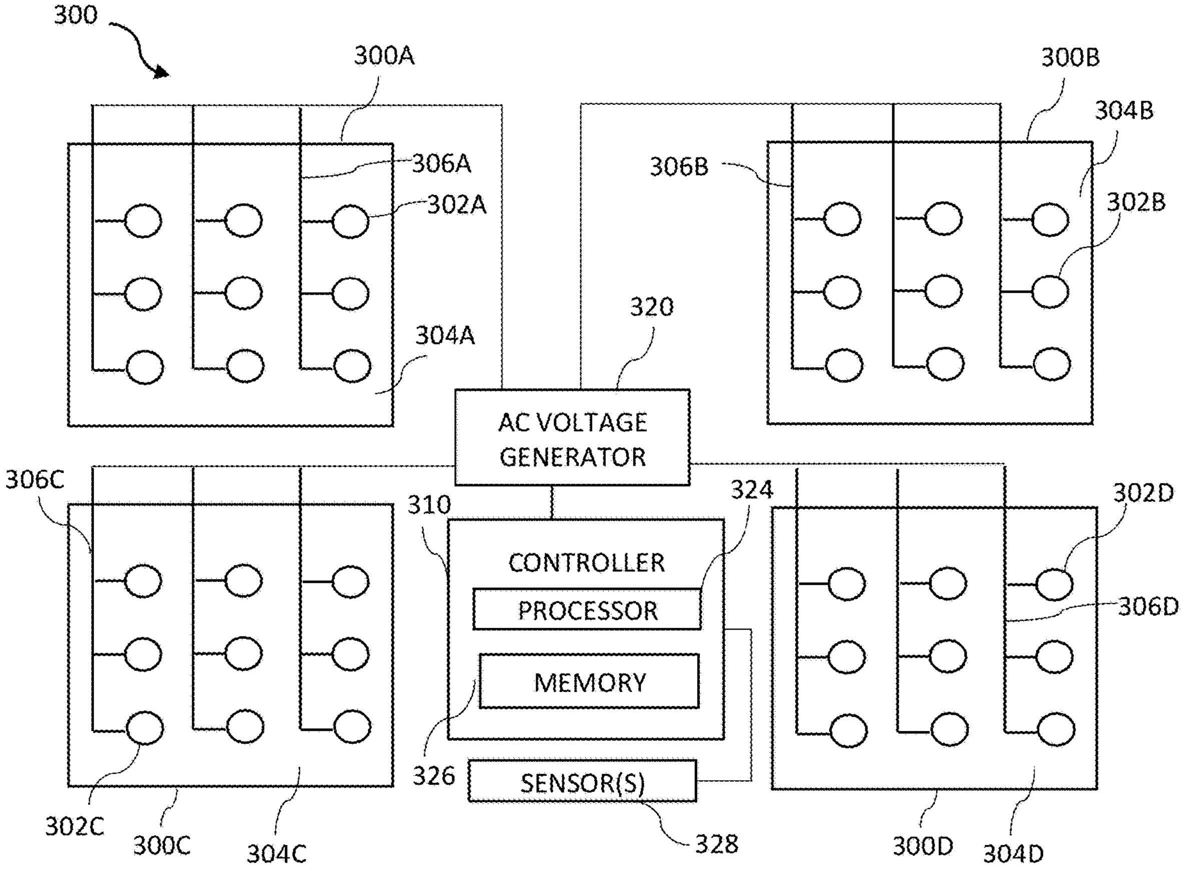
FIG. 3 depicts an example apparatus to apply alternating electric fields to the subject's body.

FIG. 3 depicts an example apparatus 300 to apply alternating electric fields (e.g., TTFields) to the subject's body. The system may be used for treating a target region of a subject's body with an alternating electric field. In an example, the target region may be in the subject's brain, and an alternating electric field may be delivered to the subject's body via two pairs of transducer arrays positioned on a head of the subject's body (such as, for example, in FIG. 5, which has four transducers 500). In another example, the target region may be in the subject's torso, and an alternating electric field may be delivered to the subject's body via two pairs of transducer arrays positioned on at least one of a thorax, an abdomen, or one or both thighs of the subject's body. Other transducer array placements on the subject's body may be possible.

The example apparatus 300 depicts an example system having four transducers (or "transducer arrays") 300A-D. Each transducer 300A-D may include substantially flat electrode elements 302A-D positioned on a substrate 304A-D and electrically and physically connected (e.g., through conductive wiring 306A-D). For each substrate 304A-D, the respective electrode elements 302A-D of the substrate may be electrically connected to each other and may be physically connected to their respective substrate 304A-D. In an example, the electrode elements 302A-D may be controlled as a collective, such that the electrode elements 302A-D receive and execute a same instruction signal. In an example, the electrode elements 302A-D may be individually controlled, such that each electrode element may receive and execute an instruction different from an instruction received and executed by another electrode element.

The substrates 304A-D may include, for example, cloth, foam, flexible plastic, and/or conductive medical gel. Two transducers (e.g., 300A and 300D) may be a first pair of transducers configured to apply an alternating electric field to a target region of the subject's body. The other two transducers (e.g., 300B and 300C) may be a second pair of transducers configured to similarly apply an alternating electric field to the target region.

The transducers 300A-D may be coupled to an AC voltage generator 320, and the system may further include a controller 310 communicatively coupled to the AC voltage generator 320. The controller 310 may include a computer having one or more processors 324 and memory 326 accessible by the one or more processors. The memory 326 may store instructions that when executed by the one or more processors control the voltage generator 320 to induce alternating electric fields between pairs of the transducers 300A-D according to one or more voltage waveforms and/or cause the computer to perform one or more methods disclosed herein. The controller 310 may monitor operations performed by the AC voltage generator 320 (e.g., via the processor(s) 324). One or more sensor(s) 328 may be coupled to the controller 310 for providing measurement values or other information to the controller 310.

The electrode elements 302A-D may be capacitively coupled. In one example, the electrode elements 302A-D are ceramic electrode elements coupled to each other via conductive wiring 306A-D. When viewed in a direction perpendicular to its face, the ceramic electrode elements may be circular shaped or non-circular shaped. In other embodiments, the array of electrode elements are not capacitively coupled, and there is no dielectric material (such as ceramic, or high dielectric polymer layer) associated with the electrode elements.

The structure of the transducers 300A-D may take many forms. The transducers may be affixed to the subject's body or attached to or incorporated in clothing covering the subject's body. The transducer may include suitable materials for attaching the transducer to the subject's body. For example, the suitable materials may include cloth, foam, flexible plastic, and/or a conductive medical gel. The transducer may be conductive or non-conductive.

The transducer may include any desired number of electrode elements. Various shapes, sizes, and materials may be used for the electrode elements. Any constructions for implementing the transducer (or electric field generating device) for use with embodiments of the invention may be used as long as they are capable of (a) delivering TTFields to the subject's body and (b) being positioned at the locations specified herein. In certain embodiments, at least one electrode element of the first, the second, the third, or the fourth transducer can include at least one ceramic disk that is adapted to generate an alternating electric field. In non-limiting embodiments, at least one electrode element of the first, the second, the third, or the fourth transducer includes a polymer film that is adapted to generate an alternating field.

Figure 4A:
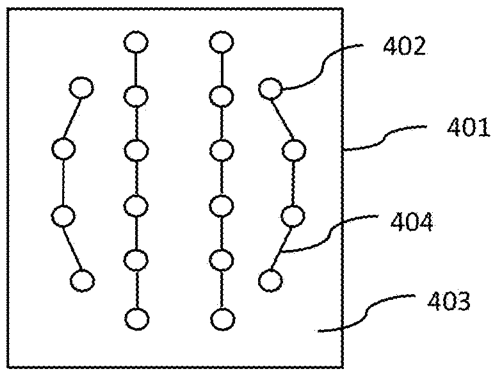
FIGS. 4A and 4B depict schematic views of exemplary designs of a transducer for applying alternating electric fields.
Figure 5:
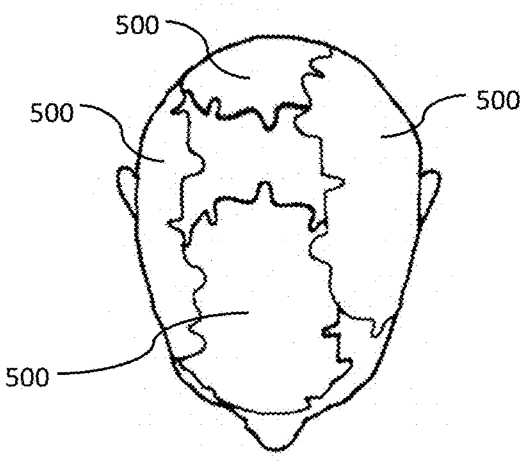
FIG. 5 depicts an example placement of transducers on a subject's head.

FIG. 4A depicts a schematic view of an exemplary design of a transducer for applying alternating electric fields. The transducer 401 includes twenty electrode elements 402, which are positioned on the substrate 403, and the electrode elements 402 are electrically and physically connected to one another through a conductive wiring 404. In some embodiments, the electrode elements 402 may include a ceramic disk.

Figure 4B:
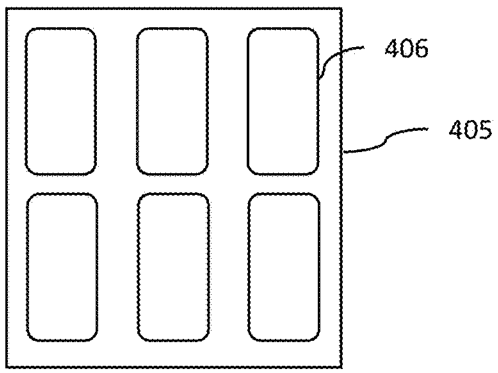

FIG. 4B depicts a schematic view of an exemplary design of a transducer for applying alternating electric fields. The transducer 405 may include one or more substantially flat electrode elements 406. In some embodiments, the electrode elements 406 are non-ceramic dielectric materials positioned over a plurality of flat conductors. Examples of non-ceramic dielectric materials positioned over flat conductors may include polymer films disposed over pads on a printed circuit board or over substantially planar pieces of metal. In an embodiment, such polymer films have a high dielectric constant, such as, for example, a dielectric constant greater than 10. In some embodiments, the electrode elements 406 may have various shapes. For example, the electrode elements may be triangular, rectangular, circular, oval, ovaloid, ovoid, or elliptical in shape or substantially triangular, substantially rectangular, substantially circular, substantially oval, substantially ovaloid, substantially ovoid, or substantially elliptical in shape. In some embodiments, each of electrode elements 406 may have a same shape, similar shapes, and/or different shapes.

Figure 6:
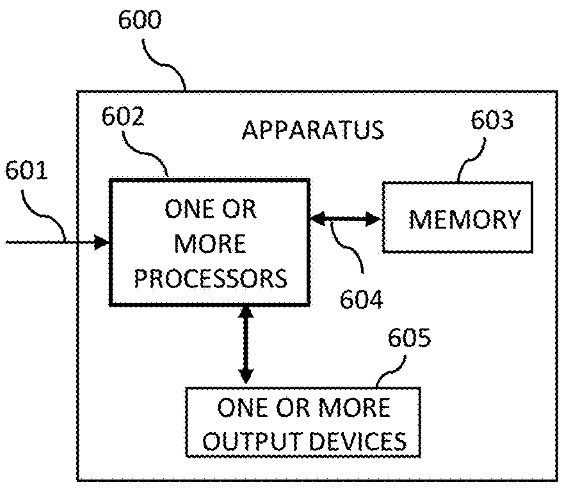
FIG. 6 depicts an example computer apparatus.

FIG. 6 depicts an example computer apparatus for use with the embodiments herein. As an example, the apparatus 600 may be a computer to implement certain inventive techniques disclosed herein, such as selecting transducer locations for delivering TTFields to the subject according to FIG. 1. For example, Steps 102 to 118 of FIG. 1 may be performed by a computer, such as computer apparatus 600. As an example, the apparatus 600 may be used as the controller 310 of FIG. 3, or as a separate computer apparatus located remote from the controller 310. For example, step 122 of FIG. 1 may be performed by a controller, such as controller 310. The apparatus 600 may include one or more processors 602, memory 603, one or more input devices, one or more input devices, and one or more output devices 605.

In one example, based on input 601, the one or more processors 602 generate control signals to control the voltage generator. In an example, the input 601 may be user input. In an example, the input 601 may be from another computer in communication with the controller apparatus 600. The input 601 may be received in conjunction with one or more input devices (not shown) of the apparatus 600.

The memory 703 is accessible by the one or more processors 602 (e.g., via a link 604) so that the one or more processors 602 may read information from and write information to the memory 603. The memory 603 may store instructions that when executed by the one or more processors 602 implement one or more methods of the present disclosure. The memory 603 may be a non-transitory computer readable medium (or a non-transitory processor readable medium) containing a set of instructions thereon for selecting at least one transducer layout for delivering tumor treating fields to a subject, wherein when executed by a processor (such as one or more processors 602), the instructions cause the processor to perform one or more methods discussed herein.

The one or more output devices 605 may provide the status of the operation of the invention, such as transducer layout selection, voltages being generated, and other operational information. The output device(s) 605 may provide visualization data according to certain embodiments described herein.

The apparatus 600 may be an apparatus for selecting at least one transducer layout for delivering tumor treating fields to a subject, the apparatus including: one or more processors (such as one or more processors 602); and memory (such as memory 603) accessible by the one or more processors, the memory storing instructions that when executed by the one or more processors, cause the apparatus to perform one or more methods described herein.

ILLUSTRATIVE EMBODIMENTS

The invention includes other illustrative embodiments ("Embodiments") as follows.

Embodiment 1: A computer-implemented method for selecting at least one transducer layout for delivering tumor treating fields to a subject, the method comprising: obtaining a three-dimensional model of the subject, the model comprising voxels; identifying a gross tumor volume for the three-dimensional model, the gross tumor volume representing a current location of a tumor in the subject; identifying a primary clinical target volume for the three-dimensional model, the primary clinical target volume having a larger volume than the gross tumor volume, the primary clinical target volume representing an approximation of the current location of the tumor in the subject; identifying a predictive clinical target volume for the three-dimensional model, the predictive clinical target volume having a larger volume than the primary clinical target volume, the predictive clinical target volume representing a predicted future location of the tumor in the subject; and selecting at least one transducer layout for delivering tumor treating fields to the subject based on the primary clinical target volume and the predictive clinical target volume.

Embodiment 2: The computer-implemented method of embodiment 1, wherein the primary clinical target volume and the gross tumor volume have approximately a same shape.

Embodiment 3: The computer-implemented method of embodiment 1, wherein a surface of the primary clinical target volume is approximately 1 mm to approximately 5 mm outside a surface of the gross tumor volume.

Embodiment 4: The computer-implemented method of embodiment 1, wherein a volume between the primary clinical target volume and the gross tumor volume is a para-tumor boundary zone.

Embodiment 5: The computer-implemented method of embodiment 1, wherein the primary clinical target volume represents a location in the subject to treat the current location of the tumor in the subject with radiation.

Embodiment 6: The computer-implemented method of embodiment 1, wherein the approximation of the current location of the tumor in the subject represented by the primary clinical target volume accounts for at least one of an error in identifying the gross tumor volume or a portion of the tumor undetected in the gross tumor volume.

Embodiment 7: The computer-implemented method of embodiment 1, wherein at least one of the primary clinical target volume and the gross tumor volume are based on user input.

Embodiment 8: The computer-implemented method of embodiment 1, wherein the predictive clinical target volume and the primary clinical target volume have different shapes.

Embodiment 9: The computer-implemented method of embodiment 1, wherein the predictive clinical target volume comprises a plurality of non-contiguous volumes.

Embodiment 10: The computer-implemented method of embodiment 1, wherein the predictive clinical target volume is based on a progression of the tumor in the subject over a period of time.

Embodiment 11: The computer-implemented method of embodiment 10, wherein the period of time is 1 months to 6 months.

Embodiment 12: The computer-implemented method of embodiment 1, wherein the predictive clinical target volume is determined using a predictive model for a tumor similar to the tumor in the subject.

Embodiment 13: The computer-implemented method of embodiment 12, wherein the predictive model determines a future location of the tumor in the subject based on a current location of the tumor and at least one of the subject's medical background, an indication or type of the tumor, a subtype or classification of the tumor, and past progression of the tumor.

Embodiment 14: The computer-implemented method of embodiment 1, wherein the predictive clinical target volume is determined using a trained machine learning model, the trained machine learning model trained to predict a future location of a tumor similar to the tumor in the subject.

Embodiment 15: The computer-implemented method of embodiment 1, further comprising: identifying a plurality of predictive clinical target volumes for the three-dimensional model, wherein the plurality of predictive clinical target volumes include the predictive clinical target volume; and assigning a weight to each of the predictive clinical target volumes, wherein each weight represents a likelihood of the predicted future location of the tumor in the subject for the respective the predictive clinical target volume, and wherein selecting at least one transducer layout for delivering tumor treating fields to the subject is based on the primary clinical target volume, the plurality of predictive clinical target volumes, and the weights for the plurality of predictive clinical target volumes.

Embodiment 16: The computer-implemented method of embodiment 15, wherein a first weight of a first predictive clinical target volume is larger than a second weight of a second predictive clinical target volume, wherein the first predictive clinical target volume is assigned a larger tumor treating fields dosage than the second predictive clinical target volume.

Embodiment 17: The computer-implemented method of embodiment 1, further comprising: identifying a differential clinical target volume as a difference between the primary clinical target volume and the predictive clinical target volume; calculating a first tumor treating fields dosage for the primary clinical target volume; calculating a second tumor treating fields dosage for the differential clinical target volume, wherein the second tumor treating fields dosage for the differential clinical target volume and the first tumor treating fields dosage for the primary clinical target volume are not identical.

Embodiment 18: The computer-implemented method of embodiment 17, wherein the second tumor treating fields dosage for the differential clinical target volume is less than the first tumor treating fields dosage for the primary clinical target volume.

Embodiment 19: The computer-implemented method of embodiment 17, wherein the second tumor treating fields dosage for the differential clinical target volume is larger than the first tumor treating fields dosage for the primary clinical target volume.

Embodiment 20: The computer-implemented method of embodiment 17, wherein the first tumor treating fields dosage for the primary clinical target volume is a pre-determined maximum dosage for tumors similar to the tumor of the subject, and the second tumor treating fields dosage for the differential clinical target volume is less than the pre-determined maximum dosage.

Embodiment 21: The computer-implemented method of embodiment 17, wherein the second tumor treating fields dosage for the differential clinical target volume is calculated as a percentage of the first tumor treating fields dosage for the primary clinical target volume.

Embodiment 22: The computer-implemented method of embodiment 17, wherein the differential clinical target volume comprises a plurality of non-contiguous volumes, wherein a tumor treating fields dosage is determined for each of the non-contiguous volumes of the differential clinical target volume, and wherein at least two of the non-contiguous volumes of the differential clinical target volume have different tumor treating fields dosages.

Embodiment 23: The computer-implemented method of embodiment 17, wherein the differential clinical target volume comprises a plurality of non-contiguous volumes, wherein a non-zero tumor treating fields dosage is determined for each of the non-contiguous volumes of the differential clinical target volume.

Embodiment 24: The computer-implemented method of embodiment 17, wherein the first tumor treating fields dosage is calculated assuming the second tumor treating fields dosage is not applied simultaneously with the first tumor treating fields dosage, and wherein the second tumor treating fields dosage is calculated assuming the first tumor treating fields dosage is not applied simultaneously with the second tumor treating fields dosage.

Embodiment 25: The computer-implemented method of embodiment 1, further comprising determining a plurality of transducer layouts for delivering tumor treating fields to the subject, wherein the at least one transducer layout is selected from the plurality of transducer layouts, wherein the transducer layouts in the plurality of transducer layouts differ by at least one of location on the subject, size of the transducer, shape of the transducer, number of electrodes of the transducer, size of electrodes of the transducer, or shape of electrodes of the transducer.

Embodiment 26: An apparatus for selecting at least one transducer layout for delivering tumor treating fields to a subject, the apparatus comprising: one or more processors; and memory accessible by the one or more processors, the memory storing instructions that when executed by the one or more processors, cause the apparatus to: obtain a three-dimensional model of the subject, the model comprising voxels; identify a gross tumor volume for the three-dimensional model, the gross tumor volume representing a current location of a tumor in the subject; identify a primary clinical target volume for the three-dimensional model, the primary clinical target volume having a larger volume than the gross tumor volume, the primary clinical target volume representing an approximation of the current location of the tumor in the subject; identify a predictive clinical target volume for the three-dimensional model, the predictive clinical target volume having a larger volume than the primary clinical target volume, the predictive clinical target volume is based on a progression of the tumor in the subject over a period of time; and select at least one transducer layout for delivering tumor treating fields to the subject based on the primary clinical target volume and the predictive clinical target volume.

Embodiment 27: A non-transitory processor readable medium for selecting at least one transducer layout for delivering tumor treating fields to a subject and containing a set of instructions thereon that when executed by a processor cause the processor to: obtain a three-dimensional model of the subject, the model comprising voxels; identify a gross tumor volume for the three-dimensional model, the gross tumor volume representing a current location of a tumor in the subject; identify a primary clinical target volume for the three-dimensional model, the primary clinical target volume having a larger volume than the gross tumor volume, the primary clinical target volume representing an approximation of the current location of the tumor in the subject; identify a predictive clinical target volume for the three-dimensional model, the predictive clinical target volume having a larger volume than the primary clinical target volume, the predictive clinical target volume representing a predicted future location of the tumor in the subject; and select at least one transducer layout for delivering tumor treating fields to the subject based on tumor treating fields dosages for the primary clinical target volume and the predictive clinical target volume.

Embodiments illustrated under any heading or in any portion of the disclosure may be combined with embodiments illustrated under the same or any other heading or other portion of the disclosure unless otherwise indicated herein or otherwise clearly contradicted by context. For example, and without limitation, embodiments described in dependent claim format for a given embodiment (e.g., the given embodiment described in independent claim format) may be combined with other embodiments (described in independent claim format or dependent claim format).

Numerous modifications, alterations, and changes to the described embodiments are possible without departing from the scope of the present invention defined in the claims. It is intended that the present invention not be limited to the described embodiments, but that it has the full scope defined by the language of the following claims, and equivalents thereof.

What is claimed is:

1. A computer-implemented method for selecting at least one transducer layout for delivering tumor treating fields to a subject, the method comprising:

obtaining, with one or more processors, a three-dimensional model of the subject, the model comprising voxels;

identifying, with the one or more processors, a gross tumor volume for the three-dimensional model, the gross tumor volume representing a current location of a tumor in the subject;

identifying, with the one or more processors, a primary clinical target volume for the three-dimensional model, the primary clinical target volume having a larger volume than the gross tumor volume, the primary clinical target volume representing an approximation of the current location of the tumor in the subject;

identifying, with the one or more processors, a predictive clinical target volume for the three-dimensional model, the predictive clinical target volume having a larger volume than the primary clinical target volume, the predictive clinical target volume representing a predicted future location of the tumor in the subject;

determining, with the one or more processors, a plurality of transducer layouts for delivering tumor treating fields to the subject;

calculating, with the one or more processors, tumor treating fields dosages for the plurality of transducer layouts based on the three-dimensional model of the subject and the predictive clinical target volume, wherein calculating the tumor treating fields dosages for the plurality of transducer layouts comprises simulating applying alternating electric fields to the three-dimensional model of the subject for each of the plurality of transducer layouts, wherein simulating applying the alternating electric fields comprises computing, for individual voxels of the three-dimensional model, electric field distributions based on electrical properties assigned to each voxel; and selecting, with the one or more processors, at least one transducer layout from the plurality of transducer layouts for delivering tumor treating fields to the subject based on the primary clinical target volume, the predictive clinical target volume, and the tumor treating fields dosages for the plurality of transducer layouts.

2. The computer-implemented method of claim 1, wherein the primary clinical target volume and the gross tumor volume have approximately a same shape.

3. The computer-implemented method of claim 1, wherein a surface of the primary clinical target volume is approximately 1 mm to approximately 5 mm outside a surface of the gross tumor volume.

4. The computer-implemented method of claim 1, wherein a volume between the primary clinical target volume and the gross tumor volume is a para-tumor boundary zone.

5. The computer-implemented method of claim 1, wherein the primary clinical target volume represents a location in the subject to treat the current location of the tumor in the subject with radiation.

6. The computer-implemented method of claim 1, wherein the approximation of the current location of the tumor in the subject represented by the primary clinical target volume accounts for at least one of an error in identifying the gross tumor volume or a portion of the tumor undetected in the gross tumor volume.

7. The computer-implemented method of claim 1, wherein the predictive clinical target volume and the primary clinical target volume have different shapes.

8. The computer-implemented method of claim 1, wherein the predictive clinical target volume comprises a plurality of non-contiguous volumes.

9. The computer-implemented method of claim 1, wherein the predictive clinical target volume is based on a progression of the tumor in the subject over a period of time.

10. The computer-implemented method of claim 1, wherein the predictive clinical target volume is determined using a predictive model for a tumor similar to the tumor in the subject.

11. The computer-implemented method of claim 10, wherein the predictive model determines a future location of the tumor in the subject based on a current location of the tumor and at least one of the subject's medical background, an indication or type of the tumor, a subtype or classification of the tumor, and past progression of the tumor.

12. The computer-implemented method of claim 1, wherein the predictive clinical target volume is determined using a trained machine learning model, the trained machine learning model is trained to predict a future location of a tumor similar to the tumor in the subject.

13. The computer-implemented method of claim 1, further comprising:

identifying a plurality of predictive clinical target volumes for the three-dimensional model, wherein the plurality of predictive clinical target volumes includes the predictive clinical target volume; and assigning a weight to each of the predictive clinical target volumes, wherein each weight represents a likelihood of the predicted future location of the tumor in the subject for the respective the predictive clinical target volume, and wherein selecting the at least one transducer layout for delivering tumor treating fields to the subject is based on the primary clinical target volume, the plurality of predictive clinical target volumes, and the weights for the plurality of predictive clinical target volumes.

14. The computer-implemented method of claim 13, wherein a first weight of a first predictive clinical target volume is larger than a second weight of a second predictive clinical target volume, wherein the first predictive clinical target volume is assigned a larger tumor treating fields dosage than the second predictive clinical target volume.

15. The computer-implemented method of claim 1, wherein generating tumor treating fields dosages for the plurality of transducer layouts based on the predictive clinical target volume comprises:

identifying a differential clinical target volume as a difference between the primary clinical target volume and the predictive clinical target volume;

calculating a first tumor treating fields dosage for the primary clinical target volume; and calculating a second tumor treating fields dosage for the differential clinical target volume, wherein the second tumor treating fields dosage for the differential clinical target volume and the first tumor treating fields dosage for the primary clinical target volume are not identical.

16. The computer-implemented method of claim 15, wherein the second tumor treating fields dosage for the differential clinical target volume is less than the first tumor treating fields dosage for the primary clinical target volume.

17. The computer-implemented method of claim 15, wherein the first tumor treating fields dosage for the primary clinical target volume is a pre-determined maximum dosage for tumors similar to the tumor of the subject, and the second tumor treating fields dosage for the differential clinical target volume is less than the pre-determined maximum dosage.

18. The computer-implemented method of claim 15, wherein the first tumor treating fields dosage is calculated assuming the second tumor treating fields dosage is not applied simultaneously with the first tumor treating fields dosage, and wherein the second tumor treating fields dosage is calculated assuming the first tumor treating fields dosage is not applied simultaneously with the second tumor treating fields dosage.

19. The computer-implemented method of claim 1, wherein identifying, with the one or more processors, the predictive clinical target volume for the three-dimensional model uses a predictive model, wherein the predictive model is a trained machine learning model that was trained to predict a future location of a tumor in a subject.

20. The computer-implemented method of claim 1, further comprising:

outputting the selected at least one transducer layout for delivering the tumor treating fields to the subject.

21. An apparatus for selecting at least one transducer layout for delivering tumor treating fields to a subject, the apparatus comprising: one or more processors; and memory accessible by the one or more processors, the memory storing instructions that when executed by the one or more processors, cause the apparatus to:

obtain a three-dimensional model of the subject, the model comprising voxels;

identify a gross tumor volume for the three-dimensional model, the gross tumor volume representing a current location of a tumor in the subject;

identify a primary clinical target volume for the three-dimensional model, the primary clinical target volume having a larger volume than the gross tumor volume, the primary clinical target volume representing an approximation of the current location of the tumor in the subject;

identify a predictive clinical target volume for the three-dimensional model, the predictive clinical target volume having a larger volume than the primary clinical target volume, the predictive clinical target volume is based on a progression of the tumor in the subject over a period of time;

determine a plurality of transducer layouts for delivering tumor treating fields to the subject;

calculate tumor treating fields dosages for the plurality of transducer layouts based on the three-dimensional model of the subject and the predictive clinical target volume, wherein calculating the tumor treating fields dosages for the plurality of transducer layouts comprises simulating applying alternating electric fields to the three-dimensional model of the subject for each of the plurality of transducer layouts, wherein simulating applying the alternating electric fields comprises computing, for individual voxels of the three-dimensional model, electric field distributions based on electrical properties assigned to each voxel; and select at least one transducer layout from the plurality of transducer layouts for delivering tumor treating fields to the subject based on the primary clinical target volume, the predictive clinical target volume, and the tumor treating fields dosages for the plurality of transducer layouts.

22. A non-transitory processor readable medium for selecting at least one transducer layout for delivering tumor treating fields to a subject and containing a set of instructions thereon that when executed by a processor cause the processor to:

obtain a three-dimensional model of the subject, the model comprising voxels;

identify a gross tumor volume for the three-dimensional model, the gross tumor volume representing a current location of a tumor in the subject;

identify a primary clinical target volume for the three-dimensional model, the primary clinical target volume having a larger volume than the gross tumor volume, the primary clinical target volume representing an approximation of the current location of the tumor in the subject;

identify a predictive clinical target volume for the three-dimensional model, the predictive clinical target volume having a larger volume than the primary clinical target volume, the predictive clinical target volume representing a predicted future location of the tumor in the subject;

determine a plurality of transducer layouts for delivering tumor treating fields to the subject;

calculate tumor treating fields dosages for the plurality of transducer layouts based on the three-dimensional model of the subject and the predictive clinical target volume, wherein calculating the tumor treating fields dosages for the plurality of transducer layouts comprises simulating applying alternating electric fields to the three-dimensional model of the subject for each of the plurality of transducer layouts, wherein simulating applying the alternating electric fields comprises computing, for individual voxels of the three-dimensional model, electric field distributions based on electrical properties assigned to each voxel; and select at least one transducer layout from the plurality of transducer layouts for delivering tumor treating fields to the subject based on tumor treating fields dosages for the primary clinical target volume, the predictive clinical target volume, and the tumor treating fields dosages for the plurality of transducer layouts.

* * * * *